United States Patent [19]

Zwarun et al.

[11] Patent Number: 4,828,797
[45] Date of Patent: May 9, 1989

[54] EO BIOLOGICAL TEST PACK

[75] Inventors: Andrew A. Zwarun, Roslyn Heights; Steven T. Buglino, Bayport, both of N.Y.

[73] Assignee: Edward Weck Incorporated, Princeton, N.J.

[21] Appl. No.: 877,947

[22] Filed: Jun. 24, 1986

[51] Int. Cl.$^4$ ............................................. G01N 21/00
[52] U.S. Cl. ........................................ 422/55; 422/58; 422/61; 422/86; 422/28; 436/1; 206/364; 206/439
[58] Field of Search ........................ 422/55, 56, 57, 58, 422/61, 86, 87, 88, 26, 102; 436/1; 206/438, 439, 363, 364, 365; 211/60.1

[56] References Cited

U.S. PATENT DOCUMENTS

| | | | |
|---|---|---|---|
| 2,720,969 | 10/1955 | Kendall | 206/365 |
| 3,032,186 | 5/1962 | Jenkins | 206/365 |
| 3,440,144 | 4/1969 | Anderson | 195/103.5 |
| 3,625,353 | 12/1971 | Ishii | 206/365 |
| 3,661,717 | 5/1972 | Nelson | 195/103.5 |
| 4,023,934 | 5/1977 | Spinner et al. | 422/86 |
| 4,197,947 | 4/1980 | Zaidi | 206/438 |
| 4,252,904 | 2/1981 | Nelson et al. | 435/294 |
| 4,292,122 | 9/1981 | Orelski | 435/31 |
| 4,304,869 | 12/1981 | Dyke | 435/296 |
| 4,355,111 | 10/1982 | Shimizu et al. | 435/243 |
| 4,366,901 | 1/1983 | Short | 206/364 |
| 4,411,163 | 10/1983 | White | 73/864.02 |
| 4,416,984 | 11/1983 | Wheeler, Jr. | 435/31 |
| 4,461,837 | 7/1984 | Karle et al. | 435/296 |
| 4,486,387 | 12/1984 | Augurt | 422/58 |
| 4,576,795 | 3/1986 | Bruso | 422/61 |
| 4,636,472 | 1/1987 | Bruso | 435/287 |

FOREIGN PATENT DOCUMENTS

| | | | |
|---|---|---|---|
| 1192525 | 8/1985 | Canada | 206/439 |
| 0485740 | 11/1917 | France | 206/365 |

OTHER PUBLICATIONS

Association for the Advancement of Medical Instrumentation, 1985, Good Hospital Practice: Performance Evaluation of Ethylene Oxide Sterilizers-Ethylene Oxide Test Packs.

Primary Examiner—David L. Lacey
Assistant Examiner—Lori-Ann Johnson
Attorney, Agent, or Firm—Lawrence S. Levinson; Robert E. Lee, Jr.

[57] ABSTRACT

A biological test pack adapted for use in testing the efficacy of an ethylene oxide sterilization process is described. The test pack is a clear plastic tray containing an sterilization sensitive ink which has been imprinted on a card which faces out of the bottom of the plastic tray. In addition, the tray contains a plastic syringe which holds a biological indicator. On top of the plastic syringe, absorbent paper is placed. The entire pack has a Tyvek sheet which seals it until it is used. The plastic tray is molded into a shape for holding the various items in particularly desirable locations. Accordingly, a disposable test pack which is uniformly manufactured and which should yield consistent results, is described. It can be used either as a general purpose routine test pack or as a validation challenge test pack.

6 Claims, 2 Drawing Sheets

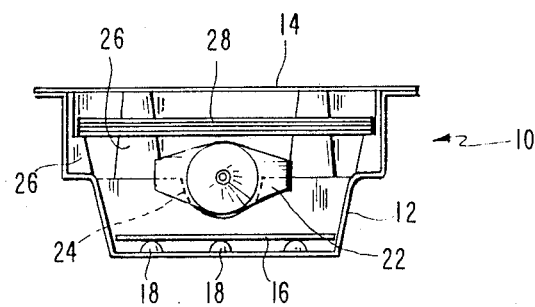
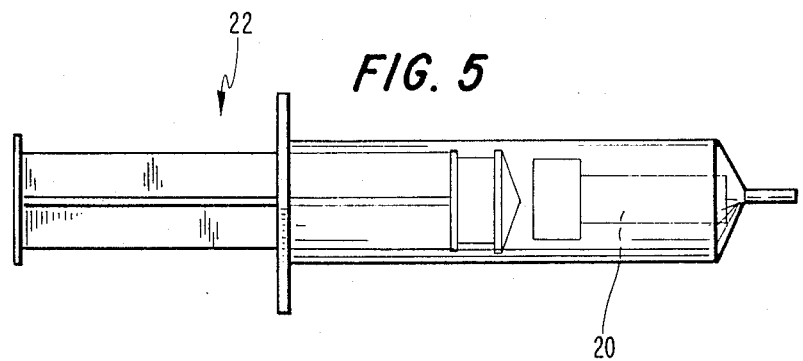

EO BIOLOGICAL TEST PACK

BACKGROUND OF THE INVENTION

The present invention relates to a biological test pack of the type used in hospital sterilization procedures. In particular, the invention relates to a biological test pack of the type used in ethylene oxide (EO) sterilization procedures.

Ethylene oxide gas is commonly used in sterilizing items for use in health care facilities. A common method of testing for the efficacy of the EO sterilization process is to include a biological indicator in the load being sterilized. A biological indicator is a suspension of a large number of bacterial spores that has been dried on a carrier, e.g., paper, and then inserted into a package, such as a glassine envelope or a plastic vial. The spore suspension is typically comprised of a bacterial species that is very resistant to EO. For example, Bacillus subtilis may be used, and it may be present on the carrier in large numbers. Accordingly, the spore suspension acts as an indicator for the effectiveness of the EO sterilization process. If large numbers of a very EO resistant organism are placed in a load, and if the sterilization process kills those resistant spores, then it is reasonable to conclude that the EO sterilization process was effective.

Since most items that are being EO sterilized are held in some sort of packaging which is intended to maintain the sterility of the contents of the pack until the time of their use, it is prudent to enclose the biological indicator inside similar packaging in order to equalize the challenge of killing the spores on the biological indicator.

In order to standardize the packaging challenge, the Association for the Advancement of Medical Instrumentation (AAMI) has issued an AAMI Recommended Practice entitled "Good Hospital Practice: Performance Evaluation of Ethylene Oxide Sterilizers—Ethylene Oxide Test Packs". That document recommends the use of a standardized routine test pack for general purpose EO sterilizers in which the biological indicator as well as a chemical indicator can be positioned, and also a more resistant challenge pack for newly installed EO sterilizers. The recommended standard challenge test packs consist of a plastic syringe enclosing a biological indicator, the syringe being wrapped in a properly-sized cotton towel, and this entire assembly enclosed inside a wrapping or pouch.

The making of an EO test pack is often a tedious process, as the test packs are laborious to construct, and not all of the necessary materials and components may be present at the institution. In addition, there is no standardized method of manufacturing or selecting the components. Compounding this problem is the fact that the surgical towel component of the test pack, which acts as a heat sink and moisture absorber in the test pack, is inherently susceptible to variation, because surgical towels are subject to large changes in their characteristics. For example, after each successive laundering, a surgical towel loses some of its fiber content and thus its capacity to provide a heat and moisture challenge. If it is laundered and then ironed, the towel may be so dry that it provides too much of a challenge to moisture absorption.

In order to minimize the above problems, it would be desirable to have an EO indicator test pack that yields the same rate of survival or death of a biological indicator as does the AAMI-described pack, but which would be fully disposable (no need to stockpile pack materials for reuse). It would also be desirable to have such a test pack be of standardized construction to eliminate variations from pack to pack, and to have it be preloaded with an appropriate biological indicator to eliminate labor required for assembly. Such a pack should behave in a manner which is equivalent to the biological indicator test pack recommended by AAMI for routine use in general purpose EO sterilizers. A challenge test pack is somewhat different from a test pack used for routine general purpose monitoring in that it provides more of a challenge to spore kill. A challenge test pack is used primarily during installation and validation of a new or repaired EO sterilizer. It is also desirable that the test pack yield results consistent with the results of the challenge test pack described by AAMI.

SUMMARY OF THE INVENTION

The present invention is a standardized, disposable ethylene oxide (EO) biological test pack consisting of a plastic tray which holds absorbent paper, a plastic syringe containing a biological indicator, and a record card preprinted with an EO-sensitive indicator. A peel back sheet is used to seal the test pack until it is used.

BRIEF DESCRIPTION OF THE DRAWINGS

FIG. 4 is a cross-sectional view of the test pack of FIG. 1 taken along the lines 4—4 of FIG. 2; and FIG. 5 is a side view of the syringe included in the test pack of the present invention.

DETAILED DESCRIPTION OF THE PREFERRED EMBODIMENT

Figure 1:
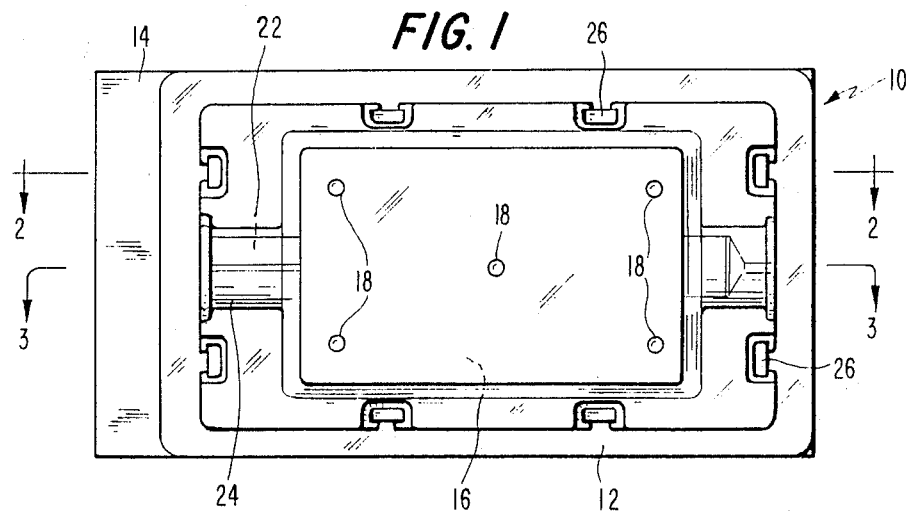
FIG. 1 is a bottom view of the test pack of the present invention.
Figure 2:
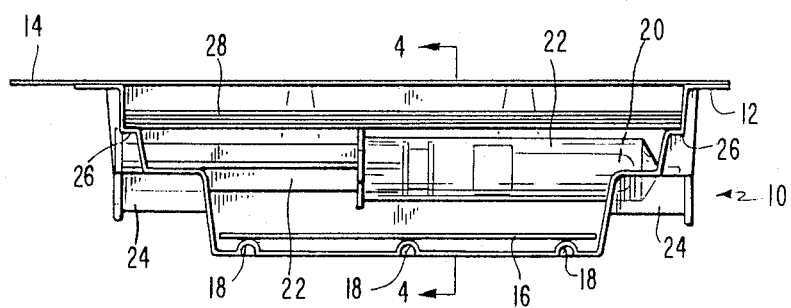
FIG. 2 is a cross-sectional view of the test pack of FIG. 1 taken along the lines 2—2 of FIG. 1.
Figure 3:
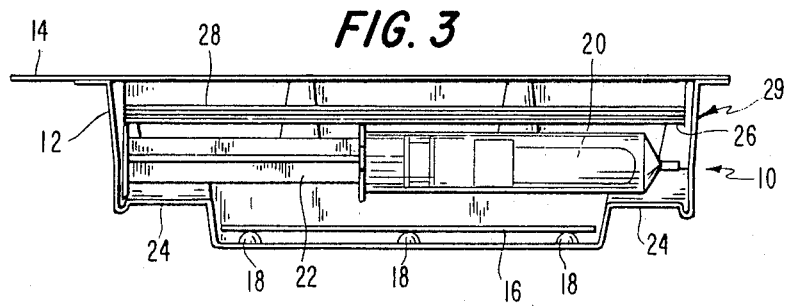
FIG. 3 is a cross-sectional view of the test pack of FIG. 1 taken along the lines 3—3 of FIG. 1.

Referring generally to FIGS. 1–5, the test pack 10 of the present invention is constructed of a clear plastic blister tray 12 which is sealed with a peel off lid 14 (shown in FIGS. 1–3), comprised of a strong, reinforced paper, such as Tyvek in the preferred embodiment of the invention. Alternatively, a paper lid can be used.

Inside the blister tray 12 is a indicator card 16 that is placed on raised bumps 18 on the bottom of the blister tray 12 in order to prevent any potential condensate from damaging the indicator card 16. The indicator card 16 is printed with an EO-sensitive ink, so it serves as both an internal indicator of the sterilization process and as a record keeping card on which the results of the biological indicator test can be recorded. The indicator card 16 can then be stored with a record keeping system after it has been exposed. By way of example, the indicator card may be of the type described in commonly assigned co-pending U.S. patent application Ser. No. 749,964 entitled Chemical Indicator which was filed on July 1, 1985 by A. A. Zwarun, S. T. Buglino, and G. L. Price and is now abandoned. Another advantage of the present design employing a clear blister tray 12 and indicator card 16 is the fact that the indicator card 16, even though located in the area that is most distant from the point of sterilant entry (the lid), is visible at all times. If, after EO processing, the ink on the indicator card 16 shows under-processing, then there would be no need to test the biological indicator 20, which is within the syringe 22. This could be a time, labor, and cost savings feature that could not be obtained if the indicator card 16 were not present, not visible, or discolored behind a tinted or hazy tray.

Above the indicator card 16 and resting in a premolded seat is the plastic syringe 22 that contains the biological indicator 20, which may be an envelope-enclosed spore strip or a self-contained biological indicator of the type known in the art or of the type disclosed in co-pending U.S. patent application Ser. No. 752,283 entitled Frangible Container With Rupturing Device which was filed on July 5, 1985 by J. R. Brown and S. T. Buglino. The design is such that the piston of the syringe 22 is required to be pulled out a certain distance if it is to fit inside the formed syringe seat 24 within the tray 12.

Resting over the syringe 22 on its own molded supports 26 are sheets of absorbent paper 28. The size, weight, and composition of the absorbent paper 28 can be used to control not only moisture absorption, but also the rate of EO entry into the pack 10. This is accomplished by the inwardly protruding supports which, together with correctly sized absorbent paper, create a rate-limiting, tortuous opening 29 through which EO can pass to the biological indicator inside the syringe.

The lid 14 seals the pack 10 and, being Tyvek in the preferred embodiment, it can withstand compression and damage and allows for easy opening of the pack. Paper can also be used, but it can tear if one test pack 10 is pressed against another's paper lid 12 or upon opening.

The present invention provides a number of advantages, as well as a method of standardizing the variability inherent in the surgical towel component of a test pack. It has been found that using 10 sheets of a certain type of absorbent paper, cut to specific dimensions, and placed one sheet on top of another yields a similar rate and amount of moisture absorption as that obtained with using the recommended 18×30 inch, all-cotton huckaback surgical towel weighing approximately 70 grams (g). One example of absorbent paper which has worked well is 100# white blotter stock paper. This particular absorbent paper cut 4"×7.5" and stacked 10 sheets high, yields approximately the same amount and rate of moisture absorption as does a 70-gram surgical towel. In this manner a test pack could be designed to mimic the moisture controlling properties of a surgical towel, but the variability associated with launderable fabrics is eliminated. In addition, absorbent paper is quite inexpensive compared to surgical towels, so it is now economical to have a disposable test pack.

If the test pack is placed vertically on its long edge, the EO sterilant can penetrate the entire Tyvek lid before it comes to the first restrictive opening—the opening between the absorbent paper sheets and the tray. In this manner the test pack acts as a routine general purpose test pack. If the test pack is placed upside-down (on its Tyvek lid), the absorbent paper rests directly on the lid and further restricts EO entry through the lid, thus increasing the resistance to EO entry into the test pack. In this configuration, the test pack acts as a challenge test pack suitable for sterilizer validation. By merely changing the positioning of the test pack, it is able to function either as a challenge test pack or as a routine general purpose test pack.

We claim:

1. A biological test pack for use in ethylene oxide sterilization processes comprising:
    (a) a clear, colorless plastic tray including syringe holding means molded therein for holding a syringe containing a biological indicator;
    (b) indicator card holding means for holding an indicator card adjacent to the bottom of said tray in a position so that the indicator card is raised away from possible condensate and is visible from outside of said tray;
    (c) absorbent paper holding means for holding absorbent paper over said syringe;
    (d) a biological indicator of the type including a glassine enclosed or a self-contained biological indicator;
    (e) a syringe containing said biological indicator, said syringe being held in place within said tray by said syringe holding means;
    (f) an indicator card having a sterilization sensitive ink imprinted thereon, said indicator card being held in said tray by said indicator card holding means with said ink imprint facing out of said tray; and
    (g) absorbent paper held in place within said tray over said syringe by said absorbent paper holding means, whereby the combination creates a rate-limiting tortuous flow path; and
    (h) means for sealing the top of said tray until it is ready for use.

2. The biological test pack of claim 1 wherein said syringe holding means is molded into said plastic tray.

3. The biological test pack of claim 2 wherein said indicator card holding means is molded into said plastic tray.

4. The biological test pack of claim 3 wherein said absorbent paper holding means is molded into said plastic tray.

5. The biological test pack of claim 4 wherein said biological indicator is a self-contained biological indicator or glassine enclosed spore strip.

6. The biological test pack of claim 5 wherein said absorbent paper is comprised of a stack of individual sheets of absorbent paper wherein said paper has an amount and rate of moisture absorption substantially equal to an all-cotton surgical towel of the type used in a standard AAMI test pack.

* * * * *